United States Patent [19]
Dijkstra

[11] 4,255,972
[45] Mar. 17, 1981

[54] DEVICE FOR THE INSPECTION OF WELDS

[75] Inventor: Durk Dijkstra, Zoetermeer, Netherlands

[73] Assignee: Rontgen Technische Dienst B.V., Rotterdam, Netherlands

[21] Appl. No.: 4,284

[22] Filed: Jan. 17, 1979

[30] Foreign Application Priority Data

Jan. 20, 1978 [NL] Netherlands ............................ 7800739

[51] Int. Cl.³ .............................................. G01N 29/04
[52] U.S. Cl. ................................................... 73/634
[58] Field of Search ................. 73/634, 633, 622, 620, 73/618, 623

[56] References Cited
U.S. PATENT DOCUMENTS

| 3,862,578 | 1/1975 | Schluter | 73/633 |
| 4,117,733 | 10/1978 | Gugel | 73/634 |

FOREIGN PATENT DOCUMENTS

| 883173 | 11/1961 | United Kingdom | 73/634 |
| 1390998 | 4/1975 | United Kingdom | 73/633 |
| 1474741 | 5/1977 | United Kingdom | 73/634 |

Primary Examiner—Stephen A. Kreitman
Attorney, Agent, or Firm—Brumbaugh, Graves, Donohue & Raymond

[57] ABSTRACT

Device for the inspection of a weld joint between a tubular stub and a wall, whereby a test probe is carrying out a rotational as well as a translational movement with respect to the stub, so that the probe is moved substantially parallel to the plane of the weld joint and the angle under which the weld joint is scanned remains substantially the same irrespective of the angle between the axis of the tubular stub and the wall.

5 Claims, 3 Drawing Figures

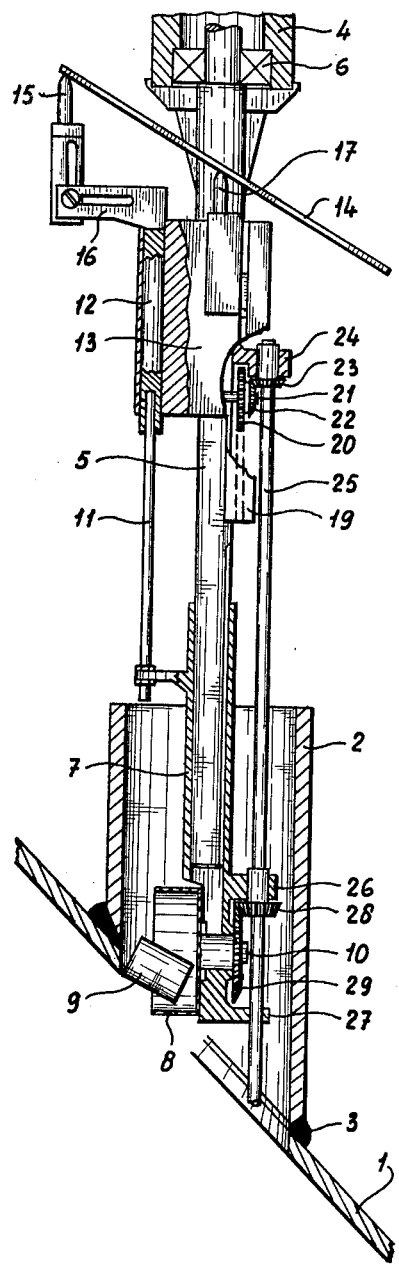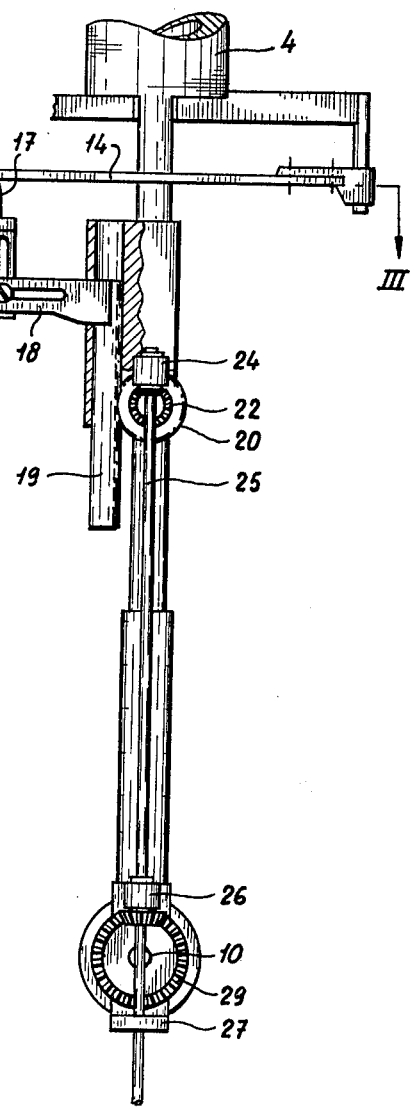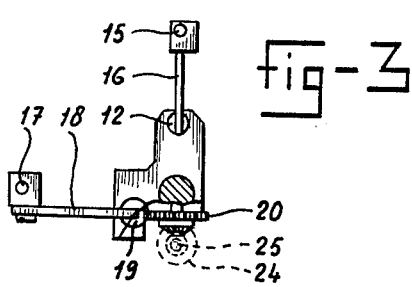

DEVICE FOR THE INSPECTION OF WELDS

BACKGROUND OF THE INVENTION

The invention relates to a device for the inspection of welds between a tubular stub and a wall, comprising a rotatably driven central shaft with a test probe, such as an ultrasonic probe, which probe can be rotated and can be moved in the axial direction of the stub.

Such a device is very well known in practice. With this the probe is gradually or continuously moved axially in respect of the stub and is rotated simultaneously.

During each revolution a given level of the weld joint is scanned so that it can be determined whether cracks or such like are present in it. In this way the weld joint is scanned over its entire height.

This does not give difficulties when the angle between the tubular stub and the wall is 90°.

In particular in case of nuclear reactor vessels, however, but also in case of steam boilers often a hemispherical or in any case an arcuate bottom and head is used, with which the tubular stubs are running parallel to each other.

This means that each tubular stub not being positioned at the same radius is positioned at an other angle to the wall. Only a centrally positioned tubular stub is situated at a right angle to the tangential plane of the top of the wall.

When, with the known device, the weld joint of a tubular stub that has to be scanned is positioned at an oblique angle, then only a part of the circumference of the weld joint is scanned at each level. So the record of the scanning has no closed formation (i.e., the probe does not follow the oblique weld along its entire path). It is thus difficult to locate the position of material defects, if any.

Further the known test probe has to be gradually or continuously moved over a great height, to wit from the heighest point of the weld joint to the opposite lying lowest point. By virtue of this, the inspection takes a rather long time. During one revolution, the angle between the centerline of the probe and the wall of the tubular stub remains the same. In case of an obliquely positioned weld joint this means that the angle between the centerline of the probe and the weld joint varies continuously. Consequently, a good inspection of the weld joint is obstructed too, because the geometry of the weld is changing continuously.

BRIEF SUMMARY OF THE INVENTION

According to the invention, all these objections are removed, because the the test probe of the invention is connected to a weld follower element which is non-rotatably connected to the shaft but is axially shiftably in respect of the shaft, a mechanism being providing for the translational movement of the test probe during a revolution of the shaft, so that the probe is moved substantially parallel to the plane of the weld, and a mechanism being provided by which the probe, during rotational and translational movement, is moved such that the angle under which the weld joint is scanned substantially remains the same.

So during each revolution of the central shaft the probe moves parallel to the plane of the weld joint, and besides this, the probe configuration always remains the same in respect of the weld joint.

In view of this the scanning is done much faster because the probe needs only to move over a distance equal to the height of the weld joint itself, measured in the axial direction of the tubular stub.

The recordings of the probe are obtained in a closed formation, the probe returning to its initial point on the weld in a single scan.

Preferably, the weld follower element is in the shape of a sleeve around the central shaft, said sleeve being connected to one end of an axially movable bar guided in a hub of the central shaft, said bar at its other end being provided with a guiding pin or roll, which during rotation of the shaft is moved by a fixedly mounted guiding plate, the slope of which depends on the angle between the tubular stub and the wall, a second guiding pin or roll co-operating with the guiding plate and acting upon the probe by means of a suitable transmission to rotate the probe around an axis lying at a right angle to the central shaft during a revolution of this central shaft.

BRIEF DESCRIPTION OF THE DRAWINGS

The invention will be described further with reference to the drawings giving an embodiment, in which:

FIG. 1 is a longitudinal section, partly in side view, of a device for the inspection of a weld joint between a tubular stub and a vessel wall situated at an angle to it;

FIG. 2 is a view of the device according to FIG. 1 seen from the right in FIG. 1; and FIG. 3 is a sectional view of the device taken along the plane III—III of FIG. 2.

DESCRIPTION OF PREFERRED EMBODIMENT

In FIG. 1 a part of the hemispherical top of a vessel is indicated by 1, the tubular stub which is welded to it is indicated by 2, and the weld joint by 3. The tubular stub, e.g., can be used for bringing control bars or such like into and out of the reactor vessel.

Because the head of a vessel substantially is hemispherical, and all tubular stubs run parallel to each other and to the longitudinal axis of the vessel, the tubular stubs, which are positioned at different distances from the vessel's longitudinal axis, are positioned at a different angle to the head 1.

The device according to the invention comprises a frame 4, which is only partly shown, and which is positioned in such a way above the tubular stub 2, that a central shaft 5 of the device according to the invention can be situated along the axis of the stub 2. The central shaft 5 is cantilevered mounted in the frame 4 by means of bearings 6.

It is obvious that the frame 4 together with the central shaft 5 has to be mounted for movement up and down to make it possible to move the central shaft 5 in and out of the tubular stub 2 and, besides this, to move it gradually or continuously axially in respect of the stub 2 during the inspection.

A tubular shaped weld follower element 7 is situated on the lower end of the central shaft 5 and is axially shiftable in respect of the shaft 5, but is non-rotatably connected with the shaft 5. A test probe holder 8 is connected to the lower end of the weld follower element 7, in which holder an ultrasonic probe head 9 is positioned. The holder 8 is rotatably mounted around a shaft 10 in the weld follower element 7. The axis of the shaft 10 is perpendicular to the axis of the shaft 5. Because the probe head 9 is not positioned in the centre of the probe holder 8, it is obvious that during rotation of the holder 8 the probe head is rotated around the axis of the shaft 10.

By means of the device according to the invention, during one revolution of the central shaft 5 the probe head will follow a path which substantially is parallel to the plane through the weld joint 3. To establish a translational movement of the weld follower element 7 during rotation of the shaft 5, the follower element 7 is connected to an axial bar 11, to the upper end of which an axially shiftable element 12 is connected, being guided in a hub 13 of the central shaft 5. It is obvious that when the element 12 is moved downwardly also the probe holder 8 and so the probe head 9 are moved downwardly. To establish the translational movement, use is made of an obliquely positioned stationary guiding plate 14. A guiding pin 15 is co-operating with the lower side of this guiding plate 14 and is connected to the element 12 by means of an arm 16. As appears from FIG. 1 the operational length of the transverse arm 16 is adjustable, as well as the length of the guiding pin 15.

In the position shown in FIG. 1, the probe head 9 is situated at about the highest place of the weld joint 3. It is obvious that when the central shaft 5 is rotated 180° the guiding pin 15 is then rotated 180° too and is engaging the lowest point of the guiding plate 14 at the right in FIG. 1. In consequence of this the probe head 9 will be situated at the lowest point of the weld joint, at the right in FIG. 1.

By a suitable selection of the angle of slope of the guiding plate 14 and of the operational length of the guiding pin 15 and the transverse arm 16 it is possible to assure that the probe head 9 follows a path which is substantially parallel to the plane of the weld joint 3 during the rotation of the central shaft 5.

Although already by this feature just described a substantial improvement is obtained in respect of the known device, which always is scanning sections perpendicular to the axis of the tubular nozzle 2, the device still needs a refinement.

The fact is that it is desirable to keep the angle between the axis of the probe head 9 and the weld joint as constant as possible during the inspection. To obtain this it is necessary that the probe head 9 is not only moved in vertical direction during the rotation of the shaft 5 but is also rotating around the axis of the horizontal shaft 10. This rotation is derived from the same guiding plate 14. To this end a second guiding pin 17 is present which is about 90° removed from the guiding pin 15 about the axis of the shaft 5.

This guiding pin 17 is connected to a rack 19 by means of a transverse arm 18. The rack 19 is also axially shiftably guided in the hub 13 of the central shaft 5. The height of the guiding pin 17 and the operative length of the transverse arm 18 again are adjustable.

A pinion 20 co-operates with the rack 19 and is freely rotatable around a horizontal shaft 21. A bevel gear 22 is secured to or integral with the pinion 20 and co-operates with a bevel gear 23, the axis of which is parallel to the axis of the central shaft 5. This bevel gear is freely rotatable supported in an extension 24 of the hub 13 by means of a tubular extension and is connected to an axial bar 25.

This axial bar 25 is rotatably supported in extensions 26 and 27 of the weld follower element 7.

In the projecting part 26 a bevel gear 28 is freely rotatable supported by means of a tubular shaped extension. This bevel gear 28 is non-rotatable connected to the bar 25, but is in axial direction shiftable in respect of this bar. This bevel gear 28 co-operates with a bevel gear 29 which is freely rotatable supported by the shaft 10 and is connected to the probe holder 8.

It is obvious that when the guiding pin 17 moves from the position shown in FIG. 1 to the right lower end of the guiding plate 14, the rack 19 will move down. Because of this the various gears will be rotated, and the probe holder will be rotated around the axis of the transverse shaft 10. By a suitable selection of the various gears it is possible to rotate the probe holder during one revolution of the central shaft 5 such that the angle at which the probe head 9 is scanning the weld joint 3 substantially remains constant.

When the device has to be used for a tubular stub positioned at another angle to the head 1 of the vessel, only the angle of slope of the guiding plate 14 has to be changed. Apart from that, the angle of slope of the guiding plate 14 need not to be exactly equal to the angle of slope of the tangential plane of the head 1. By the presence of the transverse arms 16 and 18 the angle of slope of the guiding plate 14 may differ from the angle of slope of the tangential plane. The angle of slope which is necessary, however, can be calculated without more and can be experimentally established too.

Now all weld joints of a given vessel construction can be scanned with the same device, with which it is only necessary to change the angle of slope of the guiding plate. When a tubular stub with a greater or smaller diameter has to be inspected then it may be necessary to move the probe head in radial direction.

In case of relatively large radii of curvature of a vessel head or bottom which has to be inspected, the guiding plate 14, generally speaking, may be flat. When it concerns, however, relatively small radii are concerned, then it is desirable to execute the guiding plate 14 in a curved shape.

When the device according to the invention is used, then the weld joint 3 is inspected at successive levels parallel to the plane of the weld joint 3. It is obvious that the total height over which the probe head has to be moved during the inspection is not larger than the height of the weld joint as such. In case of the known device the probe head 9 has to be moved from the highest point of the weld joint to the lowest point for example, as seen in FIG. 1 from the highest point of the illustrated weld section 3 at the left to the lowest point of the illustrated weld section 3 at the right. It is obvious that by means of the device according to the invention the inspection can be carried out much faster. Besides this, the reproduction ability is much better, because now a closed formation is scanned.

The construction is executed such that, by means of the axial bar 25, the inspection direction of the probe 9 can be quickly changed in four main directions each 90° in respect of each other.

All other inspection directions are adjustable too, by means of the same facility.

The whole device as described is suspended in a system by which the device can be situated roughly above the centre of the tubular nozzle. This system is also provided with means for an exact positioning of the inspection device.

For compensating inaccuracies in the centering of the whole device, use is made of an auxiliary probe which is mechanically connected to the extension 27. This probe continuously measures the distance between the ultrasonic probe head and the inner surface of the tubular nozzle and also supplies indications for an automatic correction should the device not have been centrally positioned.

This so-called "echo-starting device" also compensates the inaccuracy which may occur in case of tubular stubs the inner wall of which is not cylindrical.

The inspection device is intended to function in a tubular stub filled with liquid.

I claim:

1. In a device for the inspection of welds between a tubular stub and a wall, comprising a rotatably driven central shaft with a test probe, means for rotating the probe within the stub, and means for moving the probe in the axial direction of the stub; the improvement comprising means for connecting the test probe to a weld follower element which is non-rotatably connected to the shaft and is axially shiftable in respect of the shaft, means for providing translational movement of the probe axially with respect to the shaft during a revolution of the shaft to move the probe substantially parallel to the plane of the weld when the weld plane is angularly disposed at any of a number of angles with respect to the axis of the shaft, and means for maintaining the probe during rotational and translational movement at substantially the same scanning angle with respect to the weld joint.

2. A device according to claim 1 characterized in that the weld follower element is in the shape of a sleeve around the central shaft, said sleeve being connected to one end of an axially movable bar guided in a hub of the central shaft, said bar at its other end being provided with a guiding pin or roll, which during rotation of the shaft is moved by a fixedly mounted guiding plate, the slope of which depends on the angle between the tubular stub and the wall, a second guiding pin or roll being co-operating with the guiding plate and acting upon the probe by means of a suitable transmission to rotate the probe around an axis lying at a right angle to the central shaft during a revolution of this central shaft.

3. A device according to claim 2, characterized in that the transmission consists of an axially running rack which is connected to the second guiding pin or roll and is guided in the hub of the central shaft, a freely rotatable gear co-operating with said rack the shaft of which is perpendicularly positioned to the central shaft and is supported in said shaft, said gear driving a further bar running parallel to the central shaft, said further bar being connected to the probe by means of said transmission, said transmission being a movable gear transmission to rotate the probe around the axis perpendicular to the central shaft.

4. A device according to claim 2 or 3, characterized in that both the guiding pins or rolls in cirumferential direction are positioned at an angle of about 90° in respect of each other.

5. A device according to claim 4, characterized in that the guiding pins or rolls are mounted on radial transverse arms of adjustable operative length, further the level of the guiding pins or rolls being adjustable.

* * * * *